(12) United States Patent
Galli et al.

(10) Patent No.: US 7,863,290 B2
(45) Date of Patent: Jan. 4, 2011

(54) DERIVATIVES OF 5-PYRIDINYL-1-AZABICYCLO[3.2.1]OCTANE, PREPARATION METHOD THEREOF AND USE OF SAME IN THERAPEUTICS

(75) Inventors: Frederic Galli, Vaucresson (FR); Odile LeClerc, Massy (FR); Alistair Lochead, Charenton le Pont (FR); Julien Vache, Paris (FR)

(73) Assignee: sanofi-aventis, Paris (FR)

( * ) Notice: Subject to any disclaimer, the term of this patent is extended or adjusted under 35 U.S.C. 154(b) by 237 days.

(21) Appl. No.: 12/028,999

(22) Filed: Feb. 11, 2008

(65) Prior Publication Data

US 2008/0146608 A1 Jun. 19, 2008

Related U.S. Application Data

(63) Continuation of application No. PCT/FR2006/001912, filed on Aug. 7, 2006.

(30) Foreign Application Priority Data

Aug. 12, 2005 (FR) .................... 05 08528

(51) Int. Cl.
A61K 31/4745 (2006.01)
C07D 471/04 (2006.01)
(52) U.S. Cl. .................... 514/300; 546/112
(58) Field of Classification Search ............ 514/300; 546/112
See application file for complete search history.

(56) References Cited

U.S. PATENT DOCUMENTS 5,817,679 A 10/1998 Shen et al.

7,223,750 B2 * 5/2007 Galli et al. ............ 514/217.03

FOREIGN PATENT DOCUMENTS

| EP | 0664293 | 7/1995 |
| WO | WO 98/54181 | 12/1998 |
| WO | 03/057697 | * 7/2003 |
| WO | WO 03/057697 | 7/2003 |

OTHER PUBLICATIONS

Holladay, M. W., et. al., Neuronal Nicotinic Acetylchloline Receptors as Targets for Drug Discovery, Journal of Medicnal Chemistry, vol. 40, No. 26, (1997) pp. 4169-4194.

* cited by examiner

*Primary Examiner*—D. Margaret Seaman
*Assistant Examiner*—Niloofar Rahmani
(74) *Attorney, Agent, or Firm*—Balaram Gupta; Kelly L. Bender

(57) ABSTRACT

The invention relates to compounds having general formula (I), wherein R is as defined herein.

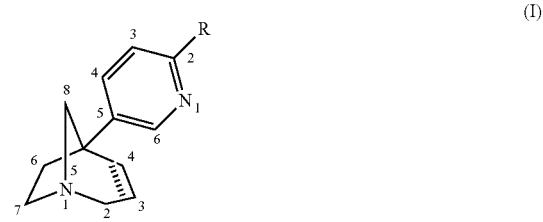

The invention also relates to acid addition salt, a hydrate or a solvate of compounds of formula (I). The invention further relates to the method of preparing said compounds and to the use of same in therapeutics.

20 Claims, No Drawings

DERIVATIVES OF 5-PYRIDINYL-1-AZABICYCLO[3.2.1]OCTANE, PREPARATION METHOD THEREOF AND USE OF SAME IN THERAPEUTICS

This application is a continuation of International application No. PCT/FR2006/001,912, filed Aug. 7, 2006, which is incorporated herein by reference in its entirety; which claims the benefit of priority of French Patent Application No. 05/08, 528, filed Aug. 12, 2005.

The present invention relates to 5-pyridyl-1-azabicyclo [3.2.1]octane derivatives, to their preparation and to their therapeutic use.

5-Pyridyl-1-azabicyclo[3.2.1]octane-based compounds are already known, described in document WO 03/057 697, with in vitro affinity for the nicotinic $\alpha_4\beta_2$ and $\alpha_7$ type receptors.

There is still a need to find and develop products with affinity for the nicotinic receptors and that are selective towards nicotinic receptors containing the $\alpha_7$ subunit.

The invention satisfies this aim by proposing novel compounds, which show good affinity for the nicotinic receptors and good selectivity towards nicotinic receptors containing the $\alpha_7$ subunit.

One subject of the present invention is compounds corresponding to the general formula (I)

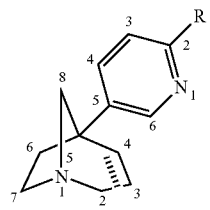

(I)

in which:
R represents a group chosen from pyrazolyl, imidazolyl, triazolyl, oxazolyl, oxadiazolyl, thiazolyl, isothiazolyl, thiadiazolyl and tetrazolyl, this group possibly being substituted with one or more groups chosen from halogen atoms and $(C_1-C_6)$alkyl, $(C_1-C_6)$alkoxy, trifluoromethoxy, trifluoromethyl, nitro, cyano, hydroxyl, amino, $(C_1-C_6)$alkylamino and di$(C_1-C_6)$alkylamino groups;
the carbon-carbon bond between positions 3 and 4 of the azabicyclooctane ring is a single or double bond.

Moreover, the carbon atom in position 5 of the azabicyclo [3.2.1]octane ring is asymmetric, and as such the compounds of the invention may exist in the form of two enantiomers or a mixture of these enantiomers. These enantiomers and the mixtures thereof, including racemic mixtures, form part of the invention.

The compounds of formula (I) may also exist in the form of bases or of acid-addition salts. Such addition salts form part of the invention.

These salts may be prepared with pharmaceutically acceptable acids, but the salts of other acids that are useful, for example for purifying or isolating the compounds of formula (I), also form part of the invention.

The compounds of formula (I) may also exist in the form of hydrates or solvates, i.e. in the form of associations or combinations with one or more water molecules or with a solvent. Such hydrates and solvates also form part of the invention.

In the context of the present invention, the following definitions apply:
a halogen atom: a fluorine, chlorine, bromine or iodine atom;
an alkyl group: a saturated linear or branched aliphatic group. Examples that may be mentioned include the following groups: methyl, ethyl, propyl, isopropyl, butyl, isobutyl, tert-butyl, pentyl, etc.;
an alkoxy group: a radical —O-alkyl in which the alkyl group is as defined above.

Among the compounds of formula (I) that are subjects of the invention, a first subgroup of compounds consists of the compounds for which:
R represents a group chosen from pyrazolyl, imidazolyl, triazolyl, oxazolyl, oxadiazolyl, thiazolyl, isothiazolyl, thiadiazolyl and tetrazolyl, this group possibly being substituted with one or more $(C_1-C_6)$alkyl groups, more particularly methyl; and
the carbon-carbon bond between positions 3 and 4 of the azabicyclooctane ring is a single or double bond.

Among the compounds of formula (I) that are subjects of the invention, a second subgroup of compounds consists of the compounds for which:
R represents a group chosen from pyrazolyl, imidazolyl, triazolyl, oxazolyl, oxadiazolyl, thiazolyl, isothiazolyl, thiadiazolyl and tetrazolyl, this group possibly being substituted with one or more $(C_1-C_6)$alkyl groups, more particularly methyl, isobutyl or n-propyl; and
the carbon-carbon bond between positions 3 and 4 of the azabicyclooctane ring is a single or double bond.

Among the compounds of formula (I) that are subjects of the invention, a third subgroup of compounds consists of the compounds for which:
R represents a group chosen from pyrazolyl, imidazolyl, triazolyl, oxazolyl, oxadiazolyl, thiazolyl and tetrazolyl, this group possibly being substituted with one or more groups chosen from halogen atoms and $(C_1-C_6)$alkyl, $(C_1-C_6)$alkoxy, trifluoromethoxy, trifluoromethyl, nitro, cyano, hydroxyl, amino, $(C_1-C_6)$alkylamino and di$(C_1-C_6)$alkylamino groups; and
the carbon-carbon bond between positions 3 and 4 of the azabicyclooctane ring is a single or double bond.

Among the compounds of formula (I) that are subjects of the invention, a fourth subgroup of compounds consists of the compounds for which:
R represents a group chosen from pyrazolyl, imidazolyl, triazolyl, oxazolyl, oxadiazolyl, thiazolyl and tetrazolyl, this group possibly being substituted with one or more $(C_1-C_6)$ alkyl groups, more particularly methyl; and
the carbon-carbon bond between positions 3 and 4 of the azabicyclooctane ring is a single or double bond.

Among the compounds of formula (I) that are subjects of the invention, a fifth subgroup of compounds consists of the compounds for which:
R represents a group chosen from pyrazolyl, imidazolyl, triazolyl, oxazolyl, oxadiazolyl, thiazolyl and tetrazolyl, this group possibly being substituted with one or more $(C_1-C_6)$ alkyl groups, more particularly methyl, isobutyl or n-propyl; and the carbon-carbon bond between positions 3 and 4 of the azabicyclooctane ring is a single or double bond.

Among the compounds of formula (I) that are subjects of the invention, a sixth subgroup of compounds consists of the compounds for which:
R represents a pyrazolyl group optionally substituted with one or more $(C_1-C_6)$alkyl, $(C_1-C_6)$alkoxy, trifluoromethoxy, trifluoromethyl, nitro, cyano, hydroxyl, amino, $(C_1-C_6)$alkylamino or di$(C_1-C_6)$alkylamino groups;

the carbon-carbon bond between positions 3 and 4 of the azabicyclooctane ring is a single or double bond.

Among the compounds of formula (I) that are subjects of the invention, a seventh subgroup of compounds consists of the compounds for which:
R represents a pyrazolyl group optionally substituted with one or more $(C_1-C_6)$alkyl groups, more particularly methyl, isobutyl or n-propyl;
the carbon-carbon bond between positions 3 and 4 of the azabicyclooctane ring is a single or double bond.

Among the compounds of formula (I) that are subjects of the invention, an eighth subgroup of compounds consists of the compounds for which:
R represents a pyrazolyl group optionally substituted with one or more $(C_1-C_6)$alkyl groups, more particularly methyl, isobutyl or n-propyl;
the carbon-carbon bond between positions 3 and 4 of the azabicyclooctane ring is a single bond.

Among the compounds of formula (I) that are subjects of the invention, mention may be made of the following specific compounds which are within the generic scope of compound of formula (I):
5-[2-(1-methyl-1H-pyrazol-4-yl)pyrid-5-yl]-1-azabicyclo [3.2.1]octane;
5-[2-(1H-pyrazol-4-yl)pyrid-5-yl]-1-azabicyclo[3.2.1]octane;
5-[2-(1H-pyrazol-4-yl)pyrid-5-yl]-1-azabicyclo[3.2.1]oct-3-ene;
5-[2-(1-methyl-1H-pyrazol-4-yl)pyrid-5-yl]-1-azabicyclo [3.2.1]-oct-3-ene;
5-[2-(1H-imidazol-1-yl)pyrid-5-yl]-1-azabicyclo[3.2.1]oct-3-ene
5-[2-(1H-imidazol-4-yl)pyrid-5-yl]-1-azabicyclo[3.2.1]oct-3-ene
5-[2-(1H-imidazol-4-yl)pyrid-5-yl]-1-azabicyclo[3.2.1]octane
5-[2-(1H-imidazol-1-yl)pyrid-5-yl]-1-azabicyclo[3.2.1]octane
5-[2-(1H-imidazol-2-yl)pyrid-5-yl]-1-azabicyclo[3.2.1]octane
5-[2-(3,5-dimethyl-1H-pyrazol-4-yl)pyrid-5-yl]-1-azabicyclo[3.2.1]octane;
5-[2-(1H-1,2,4-triazol-3-yl)pyrid-5-yl]-1-azabicyclo[3.2.1] octane;
5-[2-(5-methyl-1,2,4-oxadiazol-3-yl)pyrid-5-yl]-1-azabicyclo[3.2.1]octane;
5-[2-(1,3-oxazol-2-yl)pyrid-5-yl]-1-azabicyclo[3.2.1]octane;
5-[2-(thiazol-4-yl)pyrid-5-yl]-1-azabicyclo[3.2.1]octane
5-[2-(pyrazol-3-yl)pyrid-5-yl]-1-azabicyclo[3.2.1]octane
5-[2-(2-methylthiazol-5-yl)pyrid-5-yl]-1-azabicyclo[3.2.1] octane
5-[2-(tetrazol-5-yl)pyrid-5-yl]-1-azabicyclo[3.2.1]octane;
5-[2-(1-isobutyl-1H-pyrazol-4-yl)pyrid-5-yl]-1-azabicyclo [3.2.1]octane;
5-[2-(1-n-propyl-1H-pyrazol-4-yl)pyrid-5-yl]-1-azabicyclo [3.2.1]octane;

in the form of base or of acid-addition salt, and also in the form of hydrate or solvate; and in the form of a pure enantiomer or a mixture of enantiomers.

In the text hereinbelow, the term "protecting group" means a group that makes it possible, firstly, to protect a reactive function such as a hydroxyl or an amine during a synthesis and, secondly, to regenerate the intact reactive function at the end of the synthesis. Examples of protecting groups and of protection and deprotection methods are given in "Protective Groups in Organic Synthesis", Green et al., 2$^{nd}$ Edition (John Wiley & Sons, Inc., New York), 1991.

In the text hereinbelow, the term "leaving group" means a group that may be readily cleaved from a molecule by breaking a heterolytic bond, with loss of an electron pair. This group may thus be readily replaced with another group, for example during a substitution reaction. Such leaving groups are, for example, halogens or an activated hydroxyl group such as a methanesulfonate, benzenesulfonate, p-toluenesulfonate, triflate, acetate, etc. Examples of leaving groups and references for their preparation are given in "Advances in Organic Chemistry", J. March, 3rd Edition, Wiley Interscience, 1985, p. 310-316.

The compounds of general formula (I) may be prepared via a process illustrated according to Scheme 1 below. An addition reaction is performed on the lithiated anion of a heterocyclic compound of general formula (III), in which Z represents a bromine atom and W represents a halogen atom, in the presence of 3-oxo-1-azabicyclo[2.2.2]octane, of formula (II). The lithiated anion of the heterocyclic compound of general formula (III) is obtained by halogen-metal exchange with an alkyllithium derivative. The compound of formula (IV) is obtained and, when treated in hot acidic medium, leads to the compound of formula (V). Catalytic hydrogenation of the double bond leads to the compound of formula (VI).

The compounds of general formula (I), in which the carbon-carbon bond between positions 3 and 4 of the azabicyclooctane ring is a double bond and R represents an optionally substituted pyrazolyl, imidazolyl, triazolyl, oxazolyl, oxadiazolyl, thiazolyl, isothiazolyl, thiadiazolyl or tetrazolyl group, are obtained from the compound of formula (V) in which Z represents a bromine atom.

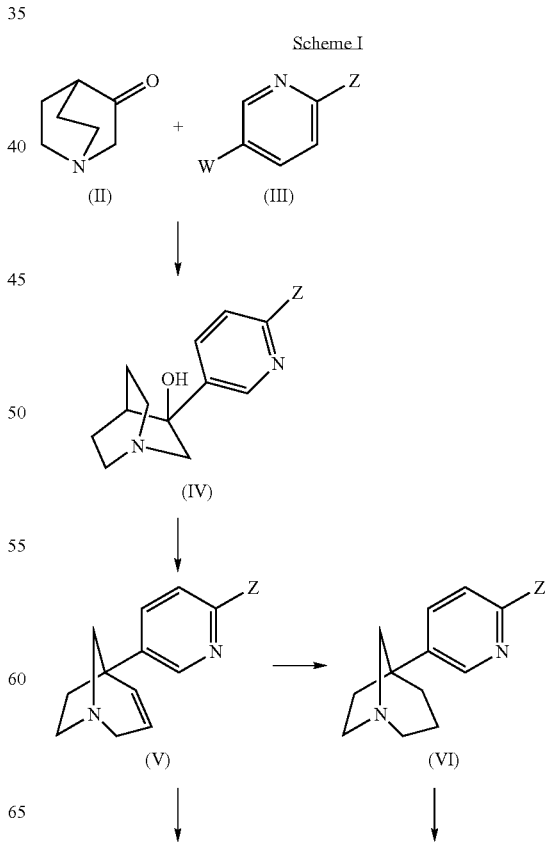

The compounds of general formula (I), in which the carbon-carbon bond between positions 3 and 4 of the azabicyclooctane ring is a single bond and R represents an optionally substituted pyrazolyl, imidazolyl, triazolyl, oxazolyl, oxadiazolyl, thiazolyl, isothiazolyl, thiadiazolyl or tetrazolyl group, are obtained from the compound of formula (VI) in which Z represents a bromine atom.

The substituent R may thus be introduced onto the compound of formula (V) or (VI) in which Z represents a bromine atom according to any method known to those skilled in the art, for instance:
- with a boronic acid of formula R—B(OH)$_2$ in which R is as defined in the general formula (I), in the presence of a palladium catalyst, for example tetrakis(triphenylphosphine)palladium;
- with a compound of formula R—H in which R is as defined in the general formula (I), in the presence of a strong base, for example sodium hydride, in a solvent, for example dimethylformamide;
- with a stannous derivative of formula R—Sn[(CH$_2$)$_3$CH$_3$)]$_3$ in which R is as defined in the general formula (I), in the presence of a palladium catalyst, for example bis(triphenylphosphino)dichloropalladium;
- with a compound of formula R—H in which R is as defined in the general formula (I), in the presence of n-butyllithium, zinc chloride and a palladium catalyst, for example tetrakis(triphenylphosphine)palladium.

The compounds of general formula (I) in which the carbon-carbon bond between positions 3 and 4 of the azabicyclooctane ring is a single bond and R represents an optionally substituted triazolyl, oxadiazolyl or tetrazolyl group may also be prepared from the compound of formula (VII).

For example:
- when R represents a triazolyl group, the compound of formula (I) may be obtained from the compound of formula (VII) in the presence of a strong base, such as a solution of sodium methoxide, and of formic hydrazide in a solvent such as methanol;
- when R represents an oxadiazolyl group, the compound of formula (I) may be obtained in two steps from the compound of formula (VII), first converted into the N-hydroxycarboxamidine of formula (VIII)

for example in the presence of hydroxylamine hydrochloride in basic medium, the compound of formula (VIII) thus obtained then reacting with acetic anhydride in a solvent such as pyridine to give the expected compound of formula (I);
- when R represents a tetrazolyl group, the compound of formula (I) may be obtained from the compound of formula (VII) in the presence of sodium azide and ammonium chloride in a solvent such as dimethylformamide.

The compound of formula (VII) is prepared from the compound of formula (VI), in which Z represents a bromine atom, for example in the presence of potassium cyanide and tetrakis(triphenylphosphine)palladium in a solvent such as dimethylformamide.

The preparation of the compound of formula (V) in which R represents a bromine atom is described in WO 03/057 697.

3-Oxo-1-azabicyclo[2.2.2]octane of formula (II) is commercially available.

The compounds of general formula (III) are commercially available or are available via methods described in the literature.

In Scheme 1, the starting compounds and the reagents, when their mode of preparation is not described, are commercially available or described in the literature, or may be prepared according to methods described therein or known to those skilled in the art.

According to another of its aspects, a subject of the invention is also the compounds of formulae (IV), (V), (VI), (VII) and (VIII). These compounds are useful as intermediates for the synthesis of the compounds of general formula (I).

The examples that follow describe the preparation of certain compounds in accordance with the invention. These examples are not limiting and merely illustrate the present invention. The compound numbers given in parentheses in the titles refer to those given in the first column of the table below, which illustrates the chemical structures and the physical properties of a few compounds according to the invention.

EXAMPLE 1

Compound 1

5-[2-(1-Methyl-1H-pyrazol-4-yl)pyrid-5-yl]-1-azabicyclo[3.2.1]octane (−)-hydrobromide (1:2)

1.1
5-(2-Bromopyrid-5-yl)-1-azabicyclo[3.2.1]octane hydrobromide (1:1)

1.95 g (7.354 mmol) of 5-(2-bromopyrid-5-yl)-1-azabicyclo[3.2.1]oct-3-ene (WO 03/057 697) are introduced into 40 ml of methanol in a hydrogenation flask, and 195 mg of platinum oxide are then placed in suspension. The medium is stirred at room temperature under a hydrogen pressure of 26 psi for 45 minutes. The reaction medium is filtered through diatomaceous earth and the solvent is removed by evaporation under reduced pressure. The residue obtained is purified by chromatography on a column of silica gel, eluting with a mixture of chloroform, methanol and aqueous ammonia in 95/5/0.5 proportions. 1.4 g of 5-(2-bromopyrid-5-yl)-1-azabicyclo[3.2.1]octane are obtained in the form of a waxy oil.

The hydrobromide salt (1:1) of 5-(2-bromopyrid-5-yl)-1-azabicyclo[3.2.1]octane is then obtained by adding 1 equivalent of a 5.7 N solution of hydrobromic acid in acetic acid. 1.82 g of expected product are obtained.

1.2 5-(2-Bromopyrid-5-yl)-1-azabicyclo[3.2.1]oc-tane (+) and (−)-hydrobromides (1:1)

The racemic mixture of 5-(2-bromopyrid-5-yl)-1-azabicyclo[3.2.1]octane hydrobromide (1:1), obtained in step 1.1, is resolved by liquid chromatography on a chiral support so as to obtain the dextrorotatory and laevorotatory enantiomers, respectively, 5-(2-bromopyrid-5-yl)-1-azabicyclo[3.2.1]octane (+)-hydrobromide (1:1) and 5-(2-bromopyrid-5-yl)-1-azabicyclo[3.2.1]octane (−)-hydrobromide (1:1).
5-(2-Bromopyrid-5-yl)-1-azabicyclo[3.2.1]octane (+)-hydrobromide (1:1): $[\alpha_D^{20}]$=+24.4° (c=1, $CH_3OH$)
5-(2-Bromopyrid-5-yl)-1-azabicyclo[3.2.1]octane (−)-hydrobromide (1:1): $[\alpha_D^{20}]$=−23.1° (c=1, $CH_3OH$)

1.3 5-[2-(1-Methyl-1H-pyrazol-4-yl)pyrid-5-yl]-1-azabicyclo-[3.2.1]octane (−)-hydrobromide (1:2)

0.162 g (0.78 mmol) of 1-methyl-4-pyrazolylboronic acid, 0.160 g (0.6 mmol) of (−)-5-(2-bromopyrid-5-yl)-1-azabicyclo[3.2.1]octane (obtained by reacting 5-(2-bromopyrid-5-yl)-1-azabicyclo[3.2.1]octane (−)-hydrobromide (1:1), prepared in step 1.2, with saturated aqueous sodium carbonate solution) are successively introduced into a 10 ml three-necked round-bottomed flask, as a solution in 3 ml of toluene and 0.3 ml of ethanol. 0.035 g (0.03 mmol) of tetrakis(triphenylphosphine)palladium and 0.6 ml of aqueous 2M sodium carbonate solution are then added and the mixture is heated at 105° C. for 18 hours. It is cooled to room temperature, the solvent is evaporated off under reduced pressure and the residue is taken up in 10 ml of chloroform and filtered through diatomaceous earth. The solvent is concentrated under reduced pressure and the residue is purified by chromatography on a column of silica gel, eluting with a mixture of chloroform, methanol and aqueous ammonia in 95/5/0.5 proportions. 0.15 g of (−)-5-[2-(1-methyl-1H-pyrazol-4-yl)pyrid-5-yl]-1-azabicyclo[3.2.1]octane is obtained, and is dissolved in 2 ml of isopropyl alcohol to add 0.196 ml of a 5.7N solution of hydrobromic acid in acetic acid. The crystals obtained are collected by filtration and dried under vacuum. 0.163 g of product is obtained.

Melting point: 259-261° C.
$^1H$ NMR (DMSO) δ (ppm): 8.50 (1H, s); 8.45 (1H, s); 8.15 (1H, s); 8.10 (1H, d); 7.95 (1H, d); 4.00 (3H, s); 3.85-3.10 (6H, m); 2.50-1.80 (6H, m).
$[\alpha_D^{20}]$=−24.4° (c=1, $CH_3OH$)

Compound 2 was prepared according to the method described in Example 1.

Compounds 3 and 4 were prepared according to the method described in Example 1, starting with 5-(2-bromopyrid-5-yl)-1-azabicyclo[3.2.1]oct-3-ene (WO 03/057 697).

Compounds 12, 13 and 15 were prepared according to the method described in Example 1, starting with (+)-5-(2-bromopyrid-5-yl)-1-azabicyclo[3.2.1]octane, obtained according to step 1.2.

EXAMPLE 2

Compound 24

5-[2-(1-Methyl-1H-pyrazol-4-yl)pyrid-5-yl]-1-azabicyclo[3.2.1]octane (+)-(S,S)-dibenzoyl tartrate (1:1)

2.1 (+/−)-5-[2-(1-Methyl-1H-pyrazol-4-yl)pyrid-5-yl]-1-azabicyclo[3.2.1]octane (compound 28)

7.08 g (34.06 mmol) of 1-methyl-4-pyrazolylboronic acid, 7.0 g (26.20 mmol) of (O)-5-(2-bromopyrid-5-yl)-1-azabicyclo[3.2.1]octane, obtained according to step 1.1 of Example 1, are successively introduced into a 250 ml three-necked round-bottomed flask, as a solution in 140 ml of toluene and 14 ml of ethanol. 1.82 g (1.57 mmol) of tetrakis(triphenylphosphine)palladium and 26.20 ml (52.40 mmol) of aqueous 2M sodium carbonate solution are then added and the mixture is heated at 90° C. for 12 hours.

The reaction medium is cooled to room temperature, poured into 50 ml of water and extracted twice with chloroform, and the combined organic phases are dried over sodium sulfate, filtered and evaporated under vacuum. The residue obtained is purified by chromatography on a column of silica gel, eluting with a mixture of chloroform, methanol and aqueous ammonia in 95/5/0.5 proportions. 5.30 g of expected product are obtained in the form of a pale yellow powder.

Melting point: 138-140° C.
$^1H$ NMR (DMSO) δ (ppm): 8.37 (1H, d); 8.19 (1H, s); 7.90 (1H, s); 7.58 (1H, dd); 7.50 (1H, dd); 3.87 (3H, s); 3.09-2.60 (6H, m); 2.21-1.31 (6H, m).

2.2 5-[2-(1-Methyl-1H-pyrazol-4-yl)pyrid-5-yl]-1-azabicyclo[3.2.1]octane (+)-(S,S)-dibenzoyl tartrate (1:1)

9.70 g (36.15 mmol) of (±)-5-[2-(1-methyl-1H-pyrazol-4-yl)pyrid-5-yl]-1-azabicyclo-[3.2.1]octane, obtained in step 2.1, are dissolved in 100 ml of ethanol in a 250 ml round-bottomed flask, 13.08 g (36.51 mmol) of (S,S)-dibenzoyltartaric acid are added and the reaction medium is stirred at room temperature for 5 minutes and concentrated under reduced pressure.

The resulting solid is dissolved in 50 ml of ethanol and then refluxed until dissolution is complete. The medium is slowly cooled to room temperature. The crystals obtained are filtered off and then dried under vacuum to give 7.10 g of the desired compound in an optical purity of 95.4%. These crystals are recrystallized under the conditions described above, in 25 ml of ethanol to give 5.54 g of 5-[2-(1-methyl-1H-pyrazol-4-yl)pyrid-5-yl]-1-azabicyclo[3.2.1]octane (+)-(S,S)-dibenzoyl tartrate (1:1) in the form of white crystals with an optical purity of 98.8%.

Melting point: 156-158° C.
$[\alpha_D^{20}]$=+78.5° (c=0.558, $CH_3OH$)

$^1$H NMR (DMSO) δ (ppm): 8.39 (s, 1H); 8.22 (s, 1H); 7.92 (s, 1H); 7.90-7.78 (m, 4H); 7.65-7.35 (m, 8H); 5.60 (s, 2H); 3.86 (s, 3H); 3.62-2.96 (m, 8H); 2.54-1.65 (m, 6H).

EXAMPLE 3

Compound 5

5-[2-(−1H-Imidazol-1-yl)pyrid-5-yl]-1-azabicyclo [3.2.1]oct-3-ene hydrobromide (1:1)

0.64 g (9.42 mmol) of imidazole dissolved in 3 ml of dimethylformamide is introduced into a 10 ml three-necked round-bottomed flask. 0.415 g (10.4 mmol) of sodium hydride as a 60% dispersion in oil is then added and the mixture is stirred at room temperature for 1 hour. The mixture is then added to a solution of 5-(2-bromopyrid-5-yl)-1-azabicyclo[3.2.1]oct-3-ene (WO 03/057 697) (0.5 g, 1.89 mmol) in dimethylformamide and the reaction medium is heated at 85° C. for 15 hours and then at 110° C. for 24 hours and the solvent is evaporated off under reduced pressure. The residue is taken up in 10 ml of chloroform and 10 ml of saturated aqueous sodium carbonate solution. The aqueous phase is extracted again with 10 ml of chloroform and the combined organic phases are washed with saturated aqueous sodium chloride solution, dried over sodium sulfate, filtered and concentrated under reduced pressure. The residue is purified by chromatography on a column of silica gel, eluting with a mixture of chloroform, methanol and aqueous ammonia in 95/5/0.5 proportions. 0.235 g of 5-[2-(−1H-imidazol-1-yl) pyrid-5-yl]-1-azabicyclo[3.2.1]oct-3-ene is obtained and is dissolved in 3 ml of isopropyl alcohol to add 0.327 ml of a 5.7N solution of hydrobromic acid in acetic acid. The crystals formed are collected by filtration and dried under vacuum.

Melting point: 233-235° C.
$^1$H NMR (DMSO) δ (ppm): 8.55 (1H, s); 8.50 (1H, s); 8.05 (1H, d); 7.95 (1H, s); 7.85 (1H, d); 7.15 (1H, s); 6.15 (1H, d); 5.75 (1H, dt); 4.20-4.10 (1H, d); 4.00-3.40 (5H, m); 2.80-2.60 (1H, t); 2.45-2.30 (1H, t).

Compound 8 was prepared according to the method described in Example 3, starting with (−)-5-(2-bromopyrid-5-yl)-1-azabicyclo[3.2.1]octane, obtained according to step 1.2 of Example 1.

Compound 11 was prepared according to the method described in Example 3, starting with (+)-5-(2-bromopyrid-5-yl)-1-azabicyclo[3.2.1]octane, obtained according to step 1.2 of Example 1.

EXAMPLE 4

Compound 6

5-[2-(−1H-Imidazol-4-yl)pyrid-5-yl]-1-azabicyclo [3.2.1]oct-3-ene hydrochloride (1:3)

4.1 5-[2-(−1-tri phenyl methylimidazol-4-yl)pyrid-5-yl]-1-azabicyclo[3.2.1]oct-3-ene 0.25 g (0.94 mmol) of 5-(2-bromopyrid-5-yl)-1-azabicyclo [3.2.1]oct-3-ene (WO 03/057 697) dissolved in 3 ml of tetrahydrofuran, 1.24 g (2.07 mmol) of 1-triphenylmethyl-4-tributylstannylimidazole and 0.06 g (0.08 mmol) of bis (triphenylphosphine)dichloropalladium are successively introduced into a 10 ml three-necked round-bottomed flask. The mixture is then heated at 85° C. for 15 hours and then diluted in 10 ml of chloroform and 10 ml of saturated aqueous sodium carbonate solution.

The aqueous phase is extracted again with 10 ml of chloroform and the combined organic phases are washed with saturated aqueous sodium chloride solution, dried over sodium sulfate, filtered and concentrated under reduced pressure. The residue is purified by chromatography on a column of silica gel, eluting with a mixture of chloroform, methanol and aqueous ammonia in 97/3/0.3 proportions. 0.36 g of expected product is obtained in the form of an amorphous solid.

4.2 5-[2-(1H-Imidazol-4-yl)pyrid-5-yl]-1-azabicyclo [3.2.1]oct-3-ene hydrochloride (1:3)

0.36 g (0.733 mmol) of 5-[2-(−1-triphenylmethylimidazol-4-yl)pyrid-5-yl]-1-azabicyclo-[3.2.1]oct-3-ene, obtained in step 4.1, dissolved in 4 ml of methanol is introduced into a 10 ml three-necked round-bottomed flask. 0.8 ml of a 6N solution of hydrochloric acid in isopropyl alcohol is then added and the reaction medium is heated at 80° C. for 3 hours. The solvent is concentrated under reduced pressure and the residue is triturated from diethyl ether. The crystals obtained are collected by filtration and dried under vacuum.

Melting point: 306-308° C.
$^1$H NMR (DMSO) δ (ppm): 11.95 (1H, s); 9.20 (1H, s); 8.65 (1H, s); 8.40 (1H, s); 8.10 (1H, d); 8.00 (1H, d); 6.20 (1H, d); 5.75 (1H, dt); 4.15 (1H, d); 3.95-3.35 (5H, m); 2.80-2.60 (1H, t); 2.45-2.30 (1H, t).

Compound 7 was prepared according to the method described in Example 4, starting with (−)-5-(2-bromopyrid-5-yl)-1-azabicyclo[3.2.1]octane, obtained according to step 1.2 of Example 1.

Compound 9 was prepared according to the method described in Example 4, starting with (+)-5-(2-bromopyrid-5-yl)-1-azabicyclo[3.2.1]octane, obtained according to step 1.2 of Example 1.

EXAMPLE 5

Compound 10

5-[2-(−1H-Imidazol-2-yl)pyrid-5-yl]-1-azabicyclo [3.2.1]octane (−)-hydrochloride (1:2)

5.1 (−)-5-[2-(−1H-Imidazol-2-yl)pyrid-5-yl]-1-azabicyclo[3.2.1]octane 1 g (5.7 mmol) of 1-(dimethylaminosulfonyl)imidazole dissolved in 9 ml of tetrahydrofuran is introduced into a 25 ml three-necked flask. The reaction medium is cooled to −78° C. and 4 ml of a 1.6M solution of n-butyllithium in hexane is added dropwise over 20 minutes. 0.73 g (5.4 mmol) of zinc chloride dissolved in 4 ml of tetrahydrofuran is then added. The mixture is stirred while allowing the temperature to return to 20° C., and 1.5 g (11.1 mmol) of zinc chloride, 0.1 g (0.09 mmol) of tetrakis(triphenylphosphine)palladium and 0.56 g (2.1 mmol) of (−)-5-(2-bromopyrid-5-yl)-1-azabicyclo[3.2.1]octane (prepared according to the method described in step 1.2 of Example 1), dissolved in 5 ml of tetrahydrofuran, are then successively added. The mixture is then refluxed for 24 hours and then cooled to room temperature. 30 ml of aqueous 30% sodium hydroxide solution and 50 ml of chloroform are added. The aqueous phase is extracted with chloroform and the combined organic phases are then washed with saturated aqueous sodium chloride solution, dried over sodium sulfate, filtered and concentrated under reduced pressure. The residue is purified by chromatography on a column of silica gel, eluting with a mixture of chloroform, methanol and aqueous ammonia in 95/5/0.5 proportions and is used in the following step without further purification.

5.2 5-[2-(-1H-Imidazol-2-yl)pyrid-5-yl]-1-azabicyclo[3.2.1]octane (−)-hydrochloride (1:2)

The product obtained in step 5.1 is dissolved in 10 ml of dioxane and 1.5 ml of aqueous 2N hydrochloric acid solution. The medium is stirred at room temperature for 2 hours and the solvent is then evaporated off under reduced pressure. The residue is taken up in 30 ml of chloroform and 30 ml of saturated aqueous sodium carbonate solution. The aqueous phase is extracted with chloroform and the combined organic phases are dried over sodium sulfate, filtered and concentrated under reduced pressure. The residue obtained is dissolved in 5 ml of isopropyl alcohol and treated with an excess of hydrochloric acid dissolved in isopropyl alcohol. The crystals obtained are collected by filtration and dried under vacuum. 0.23 g of product is obtained.

Melting point: 231-233° C.
$^1$H NMR (DMSO) δ (ppm): 11.45 (1H, s); 8.75 (1H, s); 8.55 (1H, d); 8.05 (1H, d); 7.80 (2H, s); 3.75 (1H, d); 3.60-3.10 (5H, m); 2.55-1.75 (6H, m).
$[α_D^{20}]=-34.2°$ (c=0.26, CH$_3$OH)

Compound 19 was prepared according to the method described in Example 5.

Compound 20 was prepared according to the method described in step 5.1 of Example 5 followed by a step of deprotection in basic medium, in the presence of an isovolume solution of aqueous 35% sodium hydroxide and of dioxane, at room temperature.

Compounds 18 and 21 were prepared according to the method described in step 5.1 of Example 5.

Compound 14 was prepared according to the method described in Example 5, starting with (+)-5-(2-bromopyrid-5-yl)-1-azabicyclo[3.2.1]octane, obtained according to step 1.2 of Example 1.

EXAMPLE 6

Compound 16

5-[2-(1H-1,2,4-Triazol-3-yl)pyrid-5-yl]-1-azabicyclo[3.2.1]octane (−)-hydrobromide (1:2)

6.1 (−)-(1-Azabicyclo[3.2.1]oct-5-yl)pyridine-2-carbonitrile 1.5 g (4.3 mmol) of (−)-5-(2-bromopyrid-5-yl)-1-azabicyclo[3.2.1]octane hydrobromide (prepared according to the method described in step 1.2 of Example 1), dissolved in 12 ml of dimethylformamide, 0.42 g (6.46 mmol) of potassium cyanide and 5 g (4.3 mmol) of tetrakis(triphenylphosphine) palladium are successively introduced into a 25 ml reactor. The mixture is then heated at 90° C. for 3 hours and then neutralized with saturated aqueous sodium carbonate solution. The aqueous phase is extracted with chloroform and the combined organic phases are dried over sodium sulfate, filtered and concentrated under reduced pressure. The residue is purified by chromatography on a column of silica gel, eluting with a mixture of chloroform, methanol and aqueous ammonia in 95/5/0.5 proportions. 0.705 g of expected product is thus obtained in the form of an amorphous solid.

6.2 5-[2-(1H-1,2,4-Triazol-3-yl)pyrid-5-yl]-1-azabicyclo-[3.2.1]octane (−)-hydrobromide (1:2)

0.22 g (1.03 mmol) of (−)-(1-azabicyclo[3.2.1]oct-5-yl) pyridine-2-carbonitrile, obtained in step 6.1, dissolved in 3 ml of methanol is introduced into a 10 ml reactor. The reactor is flushed with argon and 0.04 ml (0.26 mmol) of a 5.25 N solution of sodium methoxide in methanol is then added, followed, after stirring for 15 minutes at room temperature, by addition of 0.065 g (1.08 mmol) of formic hydrazide. The medium is then heated at 85° C. for 24 hours and the solvent is evaporated off. The residue is purified by chromatography on a column of silica gel, eluting with a mixture of chloroform, methanol and aqueous ammonia in 85/15/1.5 proportions. 0.155 g of (−)-5-[2-(1H-1,2,4-triazol-3-yl)pyrid-5-yl]-1-azabicyclo[3.2.1]octane is thus obtained, and is treated with 0.19 ml of a 5.7N solution of hydrobromic acid in acetic acid. The crystals obtained are collected by filtration and dried under vacuum.

Melting point: 215-217° C.
$^1$H NMR (DMSO) δ (ppm): 10.15 (1H, s); 8.65 (1H, s); 8.40 (1H, s); 8.10 (1H, d); 7.95 (1H, d); 3.80-3.10 (6H, m); 2.30-1.75 (6H, m).
$[α_D^{20}]=19.9°$ (c=1, CH$_3$OH)

Compound 22 was prepared according to the method described in Example 6, starting with (+)-(1-azabicyclo [3.2.1]oct-5-yl)pyridine-2-carbonitrile, which itself was obtained from (+)-5-(2-bromopyrid-5-yl)-1-azabicyclo [3.2.1]octane (prepared according to the method described in step 1.2 of Example 1).

EXAMPLE 7

Compound 17

5-[2-(5-Methyl-1,2,4-oxadiazol-3-yl)pyrid-5-yl]-1-azabicyclo-[3.2.1]octane (−)-hydrobromide (1:1)

7.1 (−)-5-(1-Azabicyclo[3.2.1]oct-5-yl)-N-hydroxypyridine-2-carboxamidine 0.3 g (1.4 mmol) of (−)-(1-azabicyclo[3.2.1]oct-5-yl)pyridine-2-carbonitrile, prepared according to the method described in step 6.1 of Example 5, 0.39 g (5.63 mmol) of hydroxylamine hydrochloride, 0.78 g (5.65 mmol) of potassium carbonate and 5 ml of ethyl alcohol are successively introduced into a 10 ml reactor. The mixture is refluxed for 3 hours and then filtered. The filtrate is concentrated under reduced pressure and the residue is taken up in 10 ml of water. The aqueous phase is extracted with chloroform and the combined organic phases are washed with saturated aqueous sodium chloride solution, dried over sodium sulfate and evaporated under vacuum. 0.29 g of product is thus obtained in the form of an amorphous solid.

7.2 5-[2-(5-Methyl-1,2,4-oxadiazol-3-yl)pyrid-5-yl]-1-azabicyclo[3.2.1]octane (−)-hydrobromide (1:1)

0.28 g (1.14 mmol) of (−)-5-(azabicyclo[3.2.1]oct-5-yl)-N-hydroxypyridine-2-carboximidamide, prepared in step 7.1, dissolved in 10 ml of pyridine is introduced into a 10 ml reactor. 0.1 ml (1.13 mmol) of acetic anhydride is then added and the medium is stirred at room temperature for 15 hours and then heated at 110° C. for 5 hours. The solvent is concentrated under reduced pressure and the residue is taken up in saturated aqueous sodium carbonate solution. The aqueous phase is extracted with chloroform and the combined organic phases are dried over sodium sulfate, filtered and evaporated under vacuum. The residue is purified by chromatography on a column of silica gel, eluting with a mixture of chloroform, methanol and aqueous ammonia in 96/4/0.4 proportions. 0.077 g of (−)-5-[2-(5-methyl-1,2,4-oxadiazol-3-yl)pyrid-5-yl]-1-azabicyclo[3.2.1]octane is thus obtained, and is dissolved in 1 ml of isopropyl alcohol to add 0.05 ml of a 5.7N solution of hydrobromic acid in acetic acid. The crystals obtained are collected by filtration and dried under reduced pressure.

Melting point: 321-323° C.
$^1$H NMR (DMSO) δ (ppm): 8.70 (1H, s); 8.05 (1H, d); 7.95 (1H, d); 3.80-3.20 (6H, m); 3.70 (3H, s); 2.35-1.75 (6H, m).
$[\alpha_D^{20}] = -26.4°$ (c=1, CH$_3$OH)

EXAMPLE 8

Compound 23

(+)-5-[2-(2H-tetrazol-5-yl)pyrid-5-yl]-1-azabicyclo[3.2.1]octane 0.350 g (4.64 mmol) of (+)-(1-azabicyclo[3.2.1]oct-5-yl)pyridine-2-carbonitrile (prepared according to a method similar to that described in step 6.1 of Example 6, starting with (+)-5-(2-bromopyrid-5-yl)-1-azabicyclo[3.2.1]octane obtained in step 1.2 of Example 1), 0.117 g (1.80 mmol) of sodium azide, 0.022 g (0.4 mmol) of ammonium chloride and 2 ml of dimethylformamide are successively introduced into a 10 ml reactor. The mixture is then heated at 80° C. for 15 hours and the solvent is then evaporated off under reduced pressure. The residue is taken up in methanol at room temperature. The resulting insoluble material is filtered off and the filtrate is concentrated under reduced pressure. The residue is chromatographed on a column of silica gel, eluting with a mixture of chloroform, methanol and aqueous ammonia in 80/20/2 proportions. 0.368 g of product is thus obtained in the form of crystals.

Melting point: 319-321° C.
$^1$H NMR (DMSO) δ (ppm): 8.45 (1H, s); 7.95 (1H, d); 7.70 (1H, d); 3.60-3.10 (6H, m); 2.45-1.70 (6H, m).
$[\alpha_D^{20}] = +25.2°$ (c=0.06, DMSO)

Table 1 below illustrates the chemical structures and the physical properties of a few examples of compounds according to the invention. In this table:

- in the "DB" column, "=" means that the carbon-carbon bond between positions 3 and 4 of the azabicyclooctane ring is a double bond, and "—" means that the carbon-carbon bond between positions 3 and 4 of the azabicyclooctane ring is a single bond.
- in the "Salt" column, "—" denotes a compound in base form, "HBr" denotes a hydrobromide and "HCl" denotes a hydrochloride. The acid:base mole ratios are indicated adjacent;
- in the $[\alpha_D^{20}]$ (CH$_3$OH) column, the value indicated represents the optical rotation of the compound, the concentration in g/100 ml in methanol at which this measurement was performed being indicated in parentheses; the compounds for which no indication is given in this column are racemates.

TABLE 1

(I)

| No. | DB | R | Salt | $[\alpha_D^{20}]$ (CH$_3$OH) | m.p. (° C.) (melting point) |
|---|---|---|---|---|---|
| 1 | — | 1-CH$_3$-4-pyrazolyl | HBr 2:1 | −24.4 (c = 1) | 259-261 |
| 2 | — | 4-pyrazolyl | HBr 1:1 | — | 293-295 |
| 3 | = | 4-pyrazolyl | HBr 2:1 | — | 322-324 |
| 4 | = | 1-CH$_3$-4-pyrazolyl | HBr 2:1 | — | 294-296 |
| 5 | = | 1-imidazolyl | HBr 1:1 | — | 233-235 |
| 6 | = | 4-imidazolyl | HCl 3:1 | — | 306-308 |
| 7 | — | 4-imidazolyl | HCl 3:1 | −24.8 (c = 0.8) | 292-294 |
| 8 | — | 1-imidazolyl | HBr 1:1 | −14.2 (c = 0.9) | 191-193 |
| 9 | — | 4-imidazolyl | HCl 2:1 | +23.6 (c = 1) | 288-290 |
| 10 | — | 2-imidazolyl | HCl 2:1 | −34.2 (c = 0.26) | 231-233 |
| 11 | — | 1-imidazolyl | HBr 1:1 | +22.2 (c = 1) | 233-235 |
| 12 | — | 4-pyrazolyl | HBr 2:1 | +23.6 (c = 1) | 285-287 |
| 13 | — | 1-CH$_3$-4-pyrazolyl | HBr 2:1 | +22.1 (c = 1) | 247-249 |
| 14 | — | 2-imidazolyl | HBr 2:1 | +18.3 (c = 1) | 234-236 |
| 15 | — | 3,5-(CH$_3$)$_2$-4-pyrazolyl | HBr 2:1 | +19.6 (c = 1) | 321-323 |
| 16 | — | 3-(1,2,4-triazolyl) | HBr 2:1 | −19.9 (c = 1) | 215-217 |
| 17 | — | 3-(5-CH$_3$-1,2,4-oxadiazolyl) | HBr 1:1 | −26.4 (c = 1) | 321-323 |
| 18 | — | 2-(1,3-oxazolyl) | — | −37.5 (c = 0.4) | 115-117 |
| 19 | — | 4-thiazolyl | HBr 1:1 | −27.7 (c = 1) | 272-274 |
| 20 | — | 3-pyrazolyl | HBr 1:1 | +23.8 (c = 0.38) | 273-275 |
| 21 | — | 2-CH$_3$-5-thiazolyl | HBr 1:1 | −23.2 (c = 0.36) | 267-269 |
| 22 | — | 3-(1,2,4-triazolyl) | HBr 2:1 | +20.5 (c = 1) | 215-217 |
| 23 | — | 5-tetrazolyl | — | +25.2 (c = 0.06)* | 319-321 |
| 24 | — | 1-CH$_3$-4-pyrazolyl | (S,S)-Dibenzoyl tartrate 1:1 | +78.5 (c = 0.558) | 156-158 |
| 25 | — | 1-CH$_3$-4-pyrazolyl | — | +36.1 (c = 0.49) | 142-144 |
| 26 | — | 1-CH$_3$-4-pyrazolyl | Fumarate 1:1 | +17.4 (c = 0.55) | 200-202 |
| 27 | — | 1-CH$_3$-4-pyrazolyl | HCl 2:1 | +29.4 (c = 0.48) | 191-193 |
| 28 | — | 1-CH$_3$-4-pyrazolyl | — | — | 138-140 |

TABLE 1-continued (I)

[Chemical structure diagram of compound with pyridine ring and bicyclic amine]

| No. | DB | R | Salt | $[\alpha_D^{20}]$ (CH$_3$OH) | m.p. (° C.) (melting point) |
|---|---|---|---|---|---|
| 29 | — | 1-isobutyl-4-pyrazolyl | HBr 2:1 | −24.7 (c = 1) | 104-106 |
| 30 | — | 1-n-propyl-4-pyrazolyl | HBr 2:1 | −21.8 (c = 1) | 190-192 |

*solvent: DMSO

The compounds of the invention underwent pharmacological tests that demonstrated their value as active substances of medicaments.

The compounds of the invention were thus studied as regards their affinity for nicotinic receptors containing the $\alpha_7$ subunit, according to the methods described by Mark and Collins, *J. Pharmacol. Exp. Ther.* (1982), 22, 564 and Marks et al., *Mol. Pharmacol.* (1986), 30, 427.

Male OFA rats weighing 150 to 200 g are decapitated, the entire brain is removed quickly and homogenized using a Polytron™ mill in 15 volumes of a 0.32 M sucrose solution at 4° C., followed by centrifugation at 1000×g for 10 min. The pellet is discarded and the supernatant is centrifuged at 8000×g for 20 min at 4° C. The pellet is recovered and homogenized using a Polytron™ mill in 15 volumes of double-distilled water at 4° C., followed by centrifugation at 8000×g for 20 min. The pellet is discarded and the supernatant and the buffy coat are centrifuged at 40 000×g for 20 min. The pellet is recovered, resuspended with 15 volumes of double-distilled water at 4° C. and centrifuged again at 40 000×g for 20 min, before storing it at −80° C.

On the day of the experiment, the tissue is thawed slowly and suspended in 5 volumes of buffer. 150 µl of this membrane suspension is preincubated at 37° C. for 30 min, in the dark, in the presence or absence of the test compound. Next, the membranes are incubated for 60 min at 37° C., in the dark, in the presence of 50 µl of 1 nM [$^3$H]-$\alpha$-bungarotoxin in a final volume of 250 µl of 20 mM HEPES buffer. The reaction is stopped by filtration through Whatman GF/C™ filters pretreated for 3 hours with 0.05% polyethyleneimine. The filters are rinsed with 2×5 ml of buffer at 4° C. and the radioactivity retained on each filter is measured by liquid scintigraphy. The non-specific binding in the presence of $\alpha$-bungarotoxin at 1 µM final is determined; the non-specific binding represents about 60% of the total binding recovered on the filter. For each concentration of test compound, the percentage of inhibition of the specific binding of [$^3$H]-$\alpha$-bungarotoxin is determined, followed by calculation of the IC$_{50}$ value, which is the concentration of compound that inhibits the specific binding by 50%.

The IC$_{50}$ values for the most affine compounds of the invention are between 0.001 and 1 µM.

The compounds of the invention were also studied as regards their affinity for nicotinic receptors containing the $\alpha_4\beta_2$ subunit according to the methods described by Anderson and Arneric, *Eur. J. Pharmacol* (1994), 253, 261, and by Hall et al., *Brain Res.* (1993), 600, 127.

Male Sprague Dawley rats weighing 150 to 200 g are decapitated and the entire brain is removed quickly, homogenized in 15 volumes of 0.32 M sucrose solution at 4° C. and then centrifuged at 1000×g for 10 min. The pellet is discarded and the supernatant is centrifuged at 20 000×g for 20 min at 4° C. The pellet is recovered and homogenized using a Polytron™ mill in 15 volumes of double-distilled water at 4° C., followed by centrifugation at 8000×g for 20 min. The pellet is discarded and the supernatant and the buffy coat are centrifuged at 40 000×g for 20 min, the pellet is recovered, resuspended in 15 ml of double-distilled water and centrifuged again at 40 000×g, before being stored at −80° C.

On the day of the experiment, the tissue is thawed slowly and suspended in 3 volumes of buffer. 150 µl of this membrane suspension are incubated at 4° C. for 120 min in the presence of 100 µl of 1 nM [$^3$H]-cytisine in a final volume of 500 µl of buffer, in the presence or absence of test compound. The reaction is stopped by filtration on Whatman GF/B™ filters pretreated with polyethyleneimine, the filters are rinsed with 2×5 ml of buffer at 4° C. and the radioactivity retained on the filter is measured by liquid scintigraphy. The non-specific binding is determined in the presence of 10 µM (−)-nicotine; the non-specific binding represents 75 to 85% of the total binding recovered on the filter. For each concentration of test compound, the percentage of inhibition of the specific binding of [$^3$H]-cytisine is determined, at doses of 1 µM and 10 µM. For the most affine compounds of the invention, the IC$_{50}$ value is calculated, which is the concentration of compound that inhibits the specific binding by 50%.

The IC$_{50}$ values for the most affine compounds of the invention are between 0.2 and 10 µM.

The experimental data for a few specific compounds are given in Table 2 below.

TABLE 2

| Compound No. | IC$_{50}$ $\alpha_7$ (µM) | Percentage of inhibition of the specific binding of [$^3$H]-cytisine at a dose of 1 µM, for the $\alpha_4\beta_2$ subunit (%) |
|---|---|---|
| 11 | 0.083 | 36 |
| 14 | 0.099 | 45 |
| 9 | 0.3 | 24 |

The compounds of the invention were also studied as regards to their affinity for ganglion-type peripheral nicotinic receptors according to the method described by Houghtling et al. in *Mol. Pharmacol.* 1995, 48, 280.

Bovine adrenal glands stored at −80° C. are thawed and homogenized using a Polytron™ mill in 20 volumes of 50 mM Tris-HCl at pH 7.4, and at 4° C., and are then centrifuged at 35 000×g for 10 minutes. The supernatant is removed and the pellet is resuspended in 30 volumes of 50 mM Tris-HCl buffer at 4° C. and rehomogenized, followed by recentrifuging at 35 000×g for 10 minutes. The final pellet is taken up in 10 volumes of Tris-HCl buffer at 4° C. 100 µl of membrane, i.e. 10 mg of fresh tissue, are incubated at 24° C. for 3 hours in the presence of 50 µl of 0.66 final nM [$^3$H]-epibatidine in a final volume of 250 µl of buffer, in the presence or absence of test compound. The reaction is stopped by diluting the samples with 50 µM pH 7.4 Tris-HCl buffer at 4° C., followed by filtration through Whatman GF/C™ filters pretreated for 3 hours with 0.5% polyethyleneimine. The filters are rinsed twice with 5 ml of buffer and the radioactivity retained on the filter is measured by liquid scintigraphy. The non-specific binding in the presence of 2 mM final (−)-nicotine is determined; the non-specific binding represents 30% to 40% of the total binding recovered on the filter. For each concentration of test product, the percentage of inhibition of the specific binding of [$^3$H]-epibatidine is determined, and the $IC_{50}$, the concentration of compound that inhibits 50% of the specific binding, is then calculated.

The $IC_{50}$ values for the compounds of the invention are between 1 and 10 µM.

The results obtained show that certain compounds of the invention are selective ligands for the $\alpha_7$ subunit of the nicotinic receptor and that others are mixed $\alpha_4\beta_2$ and $\alpha_7$ ligands.

These results suggest the use of the compounds in the treatment or prevention of disorders associated with dysfunction of the nicotinic receptors, especially in the central nervous system.

These disorders comprise cognitive impairment, more specifically memory impairment (acquisition, consolidation and recall), but also attention impairment, and executive function disorders associated with Alzheimer's disease, pathological ageing (Age Associated Memory Impairment, AAMI) or normal ageing (senile dementia), Parkinson's disease, trisomy 21 (Down's syndrome), psychiatric pathologies (in particular cognitive disorders associated with schizophrenia), Korsakoff's alcoholic syndrome, vascular dementia (multi-infarct dementia, MID) and cranial trauma.

The compounds of the invention may also be useful in the treatment of the motor disorders observed in Parkinson's disease or other neurological diseases such as Huntington's chorea, Tourette's syndrome, tardive dyskinesia and hyperkinesia.

They may also have neuroprotective therapeutic activity with respect to anatomo-histopathological complaints associated with the abovementioned neurodegenerative diseases.

The compounds of the invention can also constitute a curative or symptomatic treatment for strokes and cerebral hypoxic episodes. They may be used in cases of psychiatric pathologies: schizophrenia (positive and/or negative symptoms), bipolar disorders, depression, anxiety, panic attacks, attention disorders with hyperactivity, and compulsive and obsessive behavior.

They can prevent the symptoms caused by withdrawal from tobacco, from alcohol or from various substances that induce dependency, such as cocaine, LSD, cannabis and benzodiazepines.

They may be useful in the treatment of pain of diverse origin (including chronic, neuropathic or inflammation-related pain).

Moreover, the compounds of the invention may be used for treating ischaemia of the lower limbs, obliterative arteritis of the lower limbs (PAD: peripheral arterial disease), cardiac ischaemia (stable angor), myocardial infarction, cardiac insufficiency, skin cicatrization deficiency of diabetic patients, and varicose ulcers of venous insufficiency.

The compounds of the invention may also be used for treating inflammatory processes of diverse origins, in particular inflammations concerning the central nervous system.

The compounds of the invention may thus be used for the preparation of medicaments, in particular medicaments that are useful in the treatment or prevention of disorders associated with dysfunction of the nicotinic receptors, especially of the disorders mentioned above.

Thus, according to another of its aspects, the invention relates to medicaments comprising a compound of formula (I), or an addition salt thereof with a pharmaceutically acceptable acid, or a hydrate or a solvate of the compound of formula (I).

These medicaments find their therapeutic use especially in the treatment or prevention of disorders associated with dysfunction of the nicotinic receptors, especially of the disorders mentioned above.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, or a hydrate or a solvate of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration the active principle of formula (I) above, or the possible salt, solvate or hydrate thereof, may be administered in unit administration form, as a mixture with standard pharmaceutical excipients, to man and animals for the prophylaxis or treatment of the above disorders or diseases.

The suitable unit forms of administration comprise oral forms such as tablets, soft or hard gel capsules, powders, granules and oral solutions or suspensions, sublingual, buccal, intratracheal, intraocular and intranasal administration forms, forms for inhalation, topical, transdermal, subcutaneous, intramuscular or intravenous administration forms, rectal administration forms and implants. For topical application, the compounds according to the invention may be used in creams, gels, ointments or lotions.

By way of example, a unit form of administration of a compound according to the invention in tablet form may comprise the following components:

| Compound according to the invention | 50.0 mg |
|---|---|
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

The said unit forms are dosed to allow a daily administration of from 0.01 to 20 mg of active principle per kg of body weight, according to the galenical form.

There may be special cases in which higher or lower dosages are appropriate; such dosages do not depart from the context of the invention. According to the usual practice, the dosage that is appropriate for each patient is determined by the doctor according to the mode of administration and the weight and response of the said patient.

According to another of its aspects, the present invention also relates to a method for treating the pathologies indicated above, which comprises the administration to a patient of an effective dose of a compound according to the invention, or a pharmaceutically acceptable salt, or hydrate or solvate thereof.

Although the invention has been illustrated by certain of the preceding examples, it is not to be construed as being limited thereby; but rather, the invention encompasses the generic area as hereinbefore disclosed. Various modifications and embodiments can be made without departing from the spirit and scope thereof.

What is claimed is:

1. A compound of formula (I):

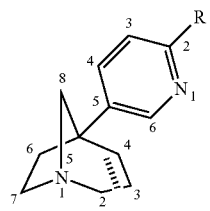

(I)

in which:
R represents a group chosen from pyrazolyl, imidazolyl, triazolyl, oxadiazolyl, thiazolyl, isothiazolyl, thiadiazolyl and tetrazolyl, said group optionally substituted with one or more groups chosen from halogen, $(C_1-C_6)$alkyl, $(C_1-C_6)$alkoxy, trifluoromethoxy, trifluoromethyl, nitro, cyano, hydroxyl, amino, $(C_1-C_6)$alkylamino and di$(C_1-C_6)$alkylamino group; and wherein
the carbon-carbon bond between positions 3 and 4 of the azabicyclooctane ring is a single or a double bond;
or an acid-addition salt thereof, a pure enantiomer or a mixture of enantiomers thereof.

2. The compound of formula (I) according to claim 1, wherein
R represents a group chosen from pyrazolyl, imidazolyl, triazolyl, oxadiazolyl, thiazolyl, isothiazolyl, thiadiazolyl and tetrazolyl, said group optionally substituted with one or more $(C_1-C_6)$alkyl group; and wherein
the carbon-carbon bond between positions 3 and 4 of the azabicyclooctane ring is a single or a double bond;
or an acid-addition salt thereof, a pure enantiomer or a mixture of enantiomers thereof.

3. The compound of formula (I) according to claim 1, wherein
R represents a group chosen from pyrazolyl, imidazolyl, triazolyl, oxadiazolyl, thiazolyl and tetrazolyl, said group optionally substituted with one or more groups chosen from halogen, $(C_1-C_6)$alkyl, $(C_1-C_6)$alkoxy, trifluoromethoxy, trifluoromethyl, nitro, cyano, hydroxyl, amino, $(C_1-C_6)$alkylamino and di$(C_1-C_6)$alkylamino group; and wherein
the carbon-carbon bond between positions 3 and 4 of the azabicyclooctane ring is a single or a double bond;
or an acid-addition salt thereof, a pure enantiomer or a mixture of enantiomers thereof.

4. The compound of formula (I) according to claim 1, wherein
R represents a group chosen from pyrazolyl, imidazolyl, triazolyl, oxadiazolyl, thiazolyl and tetrazolyl, said group optionally substituted with one or more $(C_1-C_6)$alkyl group; and wherein
the carbon-carbon bond between positions 3 and 4 of the azabicyclooctane ring is a single or a double bond;
or an acid-addition salt thereof, a pure enantiomer or a mixture of enantiomers thereof.

5. The compound of formula (I) according to claim 1, wherein
R represents a pyrazolyl group optionally substituted with one or more $(C_1-C_6)$alkyl, $(C_1-C_6)$alkoxy, trifluoromethoxy, trifluoromethyl, nitro, cyano, hydroxyl, amino, $(C_1-C_6)$alkylamino or di$(C_1-C_6)$alkylamino group; and wherein
the carbon-carbon bond between positions 3 and 4 of the azabicyclooctane ring is a single or a double bond;
or an acid-addition salt thereof, a pure enantiomer or a mixture of enantiomers thereof.

6. The compound of formula (I) according to claim 1, wherein
R represents a pyrazolyl group optionally substituted with one or more $(C_1-C_6)$alkyl group; and wherein
the carbon-carbon bond between positions 3 and 4 of the azabicyclooctane ring is a single or a double bond;
or an acid-addition salt thereof, a pure enantiomer or a mixture of enantiomers thereof.

7. The compound of formula (I) according to claim 1, wherein
R represents a pyrazolyl group optionally substituted with one or more $(C_1-C_6)$alkyl groups; and wherein
the carbon-carbon bond between positions 3 and 4 of the azabicyclooctane ring is a single bond;
or an acid-addition salt thereof, a pure enantiomer or a mixture of enantiomers thereof.

8. The compound of formula (I) according to claim 1, which is chosen from the following compounds:
5-[2-(1-methyl-1H-pyrazol-4-yl)pyrid-5-yl]-1-azabicyclo[3.2.1]octane;
5-[2-(1H-pyrazol-4-yl)pyrid-5-yl]-1-azabicyclo[3.2.1]octane;
5-[2-(1H-pyrazol-4-yl)pyrid-5-yl]-1-azabicyclo[3.2.1]oct-3-ene;
5-[2-(1-methyl-1H-pyrazol-4-yl)pyrid-5-yl]-1-azabicyclo[3.2.1]-oct-3-ene;
5-[2-(1H-imidazol-1-yl)pyrid-5-yl]-1-azabicyclo[3.2.1]oct-3-ene
5-[2-(1H-imidazol-4-yl)pyrid-5-yl]-1-azabicyclo [3.2.1]oct-3-ene
5-[2-(1H-imidazol-4-yl)pyrid-5-yl]-1-azabicyclo [3.2.1]octane
5-[2-(1H-imidazol-1-yl)pyrid-5-yl]-1-azabicyclo [3.2.1]octane
5-[2-(1H-imidazol-2-yl)pyrid-5-yl]-1-azabicyclo [3.2.1]octane
5-[2-(3,5-dimethyl-1H-pyrazol-4-yl)pyrid-5-yl]-1-azabicyclo[3.2.1]octane;
5-[2-(1H-1,2,4-triazol-3-yl)pyrid-5-yl]-1-azabicyclo[3.2.1]octane;
5-[2-(5-methyl-1,2,4-oxadiazol-3-yl)pyrid-5-yl]-1-azabicyclo[3.2.1]octane;
5-[2-(thiazol-4-yl)pyrid-5-yl]-1-azabicyclo[3.2.1]octane
5-[2-(pyrazol-3-yl)pyrid-5-yl]-1-azabicyclo[3.2.1]octane
5-[2-(2-methylthiazol-5-yl)pyrid-5-yl]-1-azabicyclo[3.2.1]octane 5-[2-(tetrazol-5-yl)pyrid-5-yl]-1-azabicyclo[3.2.1]octane;
5-[2-(1-isobutyl-1H-pyrazol-4-yl)pyrid-5-yl]-1-azabicyclo[3.2.1]octane; and
5-[2-(1-n-propyl-1H-pyrazol-4-yl)pyrid-5-yl]-1-azabicyclo[3.2.1]octane;
or an acid-addition salt thereof, a pure enantiomer or a mixture of enantiomers thereof.

9. A process for preparing a compound of formula (I) according to claim 1, comprising
reacting a compound of formula (V) or (VI):

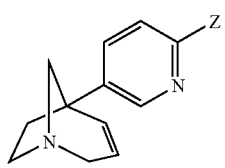
(V)

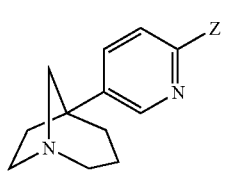
(VI)

in which Z represents a bromine atom, with a boronic acid of formula R—B(OH)$_2$ in which R is as defined in claim 1, in the presence of a palladium catalyst;
or with a compound of formula R—H in which R is as defined in claim 1, in the presence of a strong base in a solvent;
or with a stannous derivative of formula R—Sn[(CH$_2$)$_3$CH$_3$]$_3$ in which R is as defined in claim 1, in the presence of a palladium catalyst;
or with a compound of formula R—H in which R is as defined in claim 1, in the presence of n-butyllithium, zinc chloride and a palladium catalyst.

10. A process for preparing a compound of formula (I):

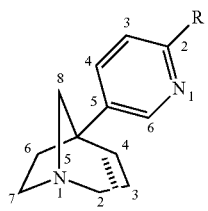
(I)

in which:
R represents a group chosen from triazolyl, oxadiazolyl and tetrazolyl, said group optionally substituted with one or more groups chosen from halogen, (C$_1$-C$_6$)alkyl, (C$_1$-C$_6$)alkoxy, trifluoromethoxy, trifluoromethyl, nitro, cyano, hydroxyl, amino, (C$_1$-C$_6$)alkylamino and di(C$_1$-C$_6$)alkylamino group; and wherein
the carbon-carbon bond between positions 3 and 4 of the azabicyclooctane ring is a single bond,
comprising
reacting a compound of formula (VI):

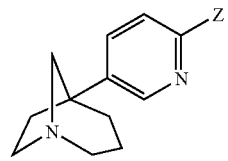
(VI)

in which Z represents a bromine atom,
with potassium cyanide in the presence of tetrakis(triphenylphosphine)palladium in a solvent to obtain a compound of formula (VII):

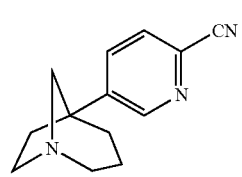
(VII)

and then
reacting the compound of formula (VII) with formic hydrazide in the presence of a strong base in a solvent when R represents a triazolyl group; or
converting the compound of formula (VII) into the N-hydroxycarboxamidine of formula (VIII) when R represents an oxadiazolyl group,

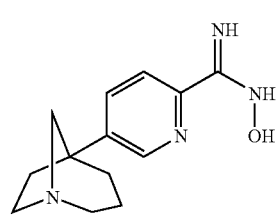
(VIII)

in the presence of hydroxylamine hydrochloride in basic medium, and then reacting compound of formula (VIII) with acetic anhydride in a solvent; or
reacting the compound of formula (VII) with sodium azide in the presence of ammonium chloride in a solvent when R represents a tetrazolyl group.

11. A compound of formula (VII):

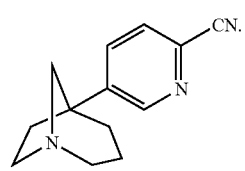
(VII)

12. A compound of formula (VIII):

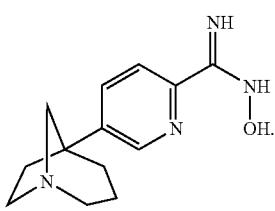

(VIII)

13. A pharmaceutical composition comprising a compound of formula (I) according to claim 1 or a pharmaceutically acceptable salt thereof in combination with at least one pharmaceutically acceptable excipient.

14. A pharmaceutical composition comprising a compound of formula (I) according to claim 2 or a pharmaceutically acceptable salt thereof in combination with at least one pharmaceutically acceptable excipient.

15. A pharmaceutical composition comprising a compound of formula (I) according to claim 3 or a pharmaceutically acceptable salt thereof in combination with at least one pharmaceutically acceptable excipient.

16. A pharmaceutical composition comprising a compound of formula (I) according to claim 4 or a pharmaceutically acceptable salt thereof in combination with at least one pharmaceutically acceptable excipient.

17. A pharmaceutical composition comprising a compound of formula (I) according to claim 5 or a pharmaceutically acceptable salt thereof in combination with at least one pharmaceutically acceptable excipient.

18. A pharmaceutical composition comprising a compound of formula (I) according to claim 6 or a pharmaceutically acceptable salt thereof in combination with at least one pharmaceutically acceptable excipient.

19. A pharmaceutical composition comprising a compound of formula (I) according to claim 7 or a pharmaceutically acceptable salt thereof in combination with at least one pharmaceutically acceptable excipient.

20. A pharmaceutical composition comprising a compound of formula (I) according to claim 8 or a pharmaceutically acceptable salt thereof in combination with at least one pharmaceutically acceptable excipient.

* * * * *

UNITED STATES PATENT AND TRADEMARK OFFICE
CERTIFICATE OF CORRECTION

| | | |
|---|---|---|
| PATENT NO. | : 7,863,290 B2 | Page 1 of 1 |
| APPLICATION NO. | : 12/028999 | |
| DATED | : January 4, 2011 | |
| INVENTOR(S) | : Frederic Galli et al. | |

It is certified that error appears in the above-identified patent and that said Letters Patent is hereby corrected as shown below:

In column 8, line 19, delete "(O)-5" and insert -- (±) -5 --, therefor.

In column 9, line 56, delete "tri phenyl methylimidazol" and insert -- triphenylmethylimidazol --, therefor.

In column 12, line 17, delete "=19.9°" and insert -- = -19.9° --, therefor.

Signed and Sealed this
Thirteenth Day of September, 2011

David J. Kappos
*Director of the United States Patent and Trademark Office*